(12) United States Patent
Vila (10) Patent No.: US 11,020,265 B2
(45) Date of Patent: Jun. 1, 2021

(54) BODY SIDE MEMBER OF AN OSTOMY APPLIANCE

(71) Applicant: Coloplast A/S, Humlebaek (DK)

(72) Inventor: Mireia Gordi Vila, London (GB)

(73) Assignee: Coloplast A/S, Humlebaek (DK)

( * ) Notice: Subject to any disclaimer, the term of this patent is extended or adjusted under 35 U.S.C. 154(b) by 361 days.

(21) Appl. No.: 15/766,366

(22) PCT Filed: Oct. 7, 2016

(86) PCT No.: PCT/DK2016/050326
§ 371 (c)(1),
(2) Date: Apr. 6, 2018

(87) PCT Pub. No.: WO2017/059869
PCT Pub. Date: Apr. 13, 2017

(65) Prior Publication Data
US 2018/0289527 A1    Oct. 11, 2018

(30) Foreign Application Priority Data

Oct. 8, 2015  (DK) ........................... PA 2015 70634
Oct. 8, 2015  (DK) ........................... PA 2015 70636

(51) Int. Cl.
*A61F 5/443*    (2006.01)
*A61F 5/445*    (2006.01)
*A61F 5/44*     (2006.01)

(52) U.S. Cl.
CPC .............. *A61F 5/443* (2013.01); *A61F 5/445* (2013.01)

(58) Field of Classification Search
CPC combination set(s) only.
See application file for complete search history.

(56) References Cited

U.S. PATENT DOCUMENTS

| 4,775,374 A | * | 10/1988 | Cilento | ............. | B29C 66/24221 |
| | | | | | 604/344 |
| 5,073,169 A | * | 12/1991 | Raiken | ................... | A61B 17/34 |
| | | | | | 604/180 |
| 5,203,806 A | * | 4/1993 | Broida | ..................... | A61F 5/445 |
| | | | | | 604/332 |
| 5,330,455 A | * | 7/1994 | McKay | .................... | A61F 5/448 |
| | | | | | 604/332 |
| 5,722,965 A | * | 3/1998 | Kuczynski | ............... | A61F 5/448 |
| | | | | | 604/344 |
| 5,730,735 A | * | 3/1998 | Holmberg | ............... | A61F 5/448 |
| | | | | | 604/338 |
| 6,071,268 A | * | 6/2000 | Wagner | ................... | A61F 5/443 |
| | | | | | 604/332 |

(Continued)

FOREIGN PATENT DOCUMENTS

CN    103281992 A    9/2013
CN    103281993 A    9/2013

(Continued)

*Primary Examiner* — Guy K Townsend
(74) *Attorney, Agent, or Firm* — Coloplast Corp., Coloplast A/S; Nick Baumann (57) ABSTRACT

A body side member of an ostomy appliance that is convertible between a first position in which a user has access to a first film layer for adhering a first adhesive to the skin surface, and a second position in which the user does not have access to the first film layer.

22 Claims, 5 Drawing Sheets

(56) References Cited

U.S. PATENT DOCUMENTS

| | | | | | |
|---|---|---|---|---|---|
| 6,312,415 | B1* | 11/2001 | Nielsen | A61F 5/443 | 604/327 |
| 6,589,222 | B1* | 7/2003 | Olsen | A61F 5/443 | 604/336 |
| 6,764,474 | B2* | 7/2004 | Nielsen | A61F 5/448 | 604/344 |
| 8,764,717 | B2* | 7/2014 | Willoughby | A61F 5/4408 | 604/337 |
| 2004/0260256 | A1* | 12/2004 | Ciok | A61F 5/445 | 604/332 |
| 2006/0184145 | A1* | 8/2006 | Ciok | A61F 5/443 | 604/338 |
| 2007/0191794 | A1* | 8/2007 | Cline | A61F 5/445 | 604/335 |
| 2007/0282284 | A1* | 12/2007 | Mullejans | A61F 5/448 | 604/333 |
| 2008/0009779 | A1* | 1/2008 | Fabo | A61F 5/443 | 602/42 |
| 2009/0131893 | A1* | 5/2009 | Priest | A61F 5/448 | 604/342 |
| 2010/0324511 | A1* | 12/2010 | Dove | A61F 5/445 | 604/342 |
| 2011/0092929 | A1* | 4/2011 | Weig | A61F 5/445 | 604/338 |
| 2011/0106032 | A1* | 5/2011 | Kratky | A61F 5/445 | 604/337 |
| 2011/0218507 | A1* | 9/2011 | Andersen | A61F 5/445 | 604/338 |
| 2012/0109086 | A1* | 5/2012 | Tsai | A61F 5/448 | 604/335 |
| 2012/0283678 | A1* | 11/2012 | Nguyen-DeMary | A61F 5/441 | 604/337 |
| 2012/0323192 | A1* | 12/2012 | Willoughby | A61F 5/44 | 604/337 |
| 2013/0053803 | A1* | 2/2013 | Willoughby | A61F 5/448 | 604/337 |
| 2014/0316360 | A1 | 10/2014 | Ekfeldt et al. | | |
| 2018/0289527 | A1* | 10/2018 | Vila | A61F 5/445 | |

FOREIGN PATENT DOCUMENTS

| | | |
|---|---|---|
| RU | 2013132977 A | 1/2015 |
| RU | 2560020 C2 | 8/2015 |
| RU | 2564083 C2 | 9/2015 |

* cited by examiner

BODY SIDE MEMBER OF AN OSTOMY APPLIANCE

SUMMARY

One aspect provides a body side member of an ostomy appliance according to the appended claim 1. Another aspect of a body side member is presented in claim 17.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Throughout this disclosure, the term "proximal" is intended to mean "towards the skin surface of a user" and the term "distal" is intended to mean "away from the skin surface of a user."

Figure 1:
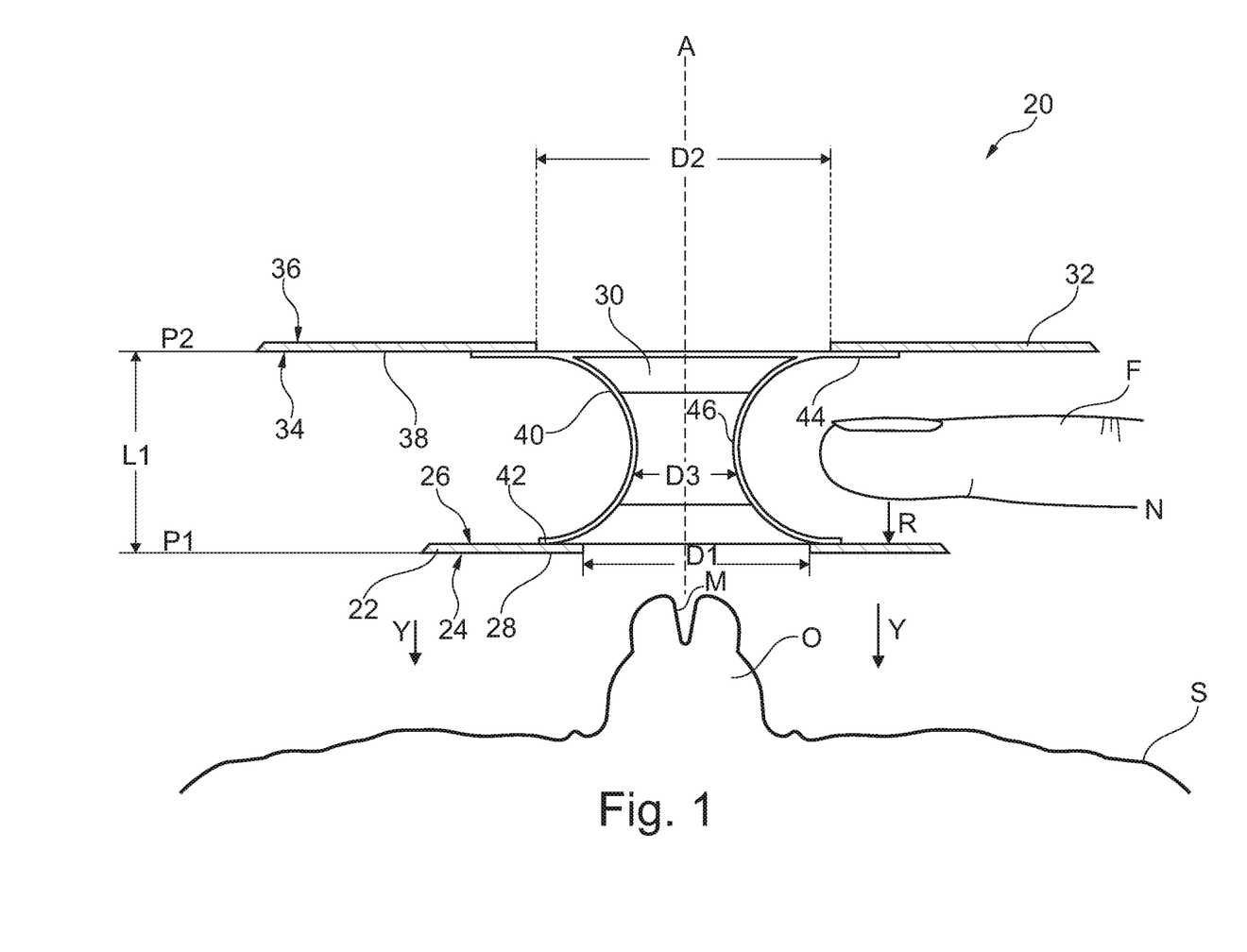
FIG. 1 is a cross-sectional view of one embodiment of a body side member in a first position, and ready to be applied to the skin surface of a user around a stoma.

FIG. 1 is a cross-sectional view of one embodiment of the body side member 20 of an ostomy appliance. The body side member 20 includes a first film layer 22 having a first proximal surface 24 and a first distal surface 26. A first adhesive 28 is provided on the first proximal surface 24 around a through-going stoma opening 30 of the body side member 20. In embodiments, the first adhesive 28 is a pressure sensitive adhesive (PSA). Suitable materials for the first adhesive 28 includes adhesives of the types disclosed in WO 2007/082538.

The body side member 20 includes a second film layer 32 having a second proximal surface 34 and a second distal surface 36. A second adhesive 38 is provided on the second proximal surface 34 around the through-going stoma opening 30 of the body side member 20. Suitable materials for the second adhesive 38 includes adhesives of the types disclosed in WO 2009/006901. In embodiments, the first adhesive 28 and the second adhesive 38 are provided at a distance L1 from each other measured along a central longitudinal axis A-A extending through the through-going stoma opening 30. In embodiments, the first adhesive 28 and the second adhesive 38 are provided such that at least a portion of the second adhesive 38 is configured to be engageable with at least a portion of the first distal surface 26 of the first film layer 22.

The body side member 20 includes a trumpet-shaped member 40 having a first end portion 42 attached to the first distal surface 26 of the first film layer 22 and a second end portion 44 attached to the second proximal surface 34 of the second film layer 32. In embodiments, each of the first end portion 42 and the second end portion 44 of the trumpet-shaped member is attached to the respective first and second film layers 22, 32 by welding. In embodiments, each of the first end portion 42 and the second end portion 44 of the trumpet-shaped member is attached to the respective first and second film layers 22, 32 with an adhesive. In the figures, the attachments between the end portions 42, 44 of the trumpet-shaped member 40 and the respective film layers 22, 32 are shown in an exaggerated manner. In one embodiment, the attachments are provided such that the film layers 22, 32 and the end portions 42, 44 of the trumpet-shaped member 40 are practically flush with each other.

In embodiments, the trumpet-shaped member 40 defines the through-going stoma opening 30 between the first film layer 22 and the second film layer 32. The trumpet-shaped member 40 thereby provides a conduit and/or pathway for the user's stoma and/or at least for the stomal output exiting the stomal meatus. In a plane of the first film layer 22 at the first proximal surface 24 the stoma opening 30 has a first diameter D1. In a plane of the second film layer 32 at the second distal surface 36 the stoma opening 30 has a second diameter D2. In one embodiment, the first diameter D1 and the second diameter D2 are different. In one embodiment, the second diameter D2 is larger than the first diameter. In one embodiment, the trumpet-shaped member 40 has an inner surface 46 and defines a third diameter D3. In one embodiment, the third diameter D3 is a minimal diameter of the through-going stoma opening 30. In embodiments, the third diameter D3 is smaller than the first diameter D1 and/or the second diameter D2.

In embodiments, the trumpet-shaped member 40 is configured to be convertible between a first position (FIG. 1) of the body side member 20, in which first position a user has finger access to the first distal surface 26 of the first film layer 22, and a second position (see FIG. 2) of the body side member 20, in which second position the user does not have finger access to the first distal surface 26 of the first film layer 22. A user's finger, such as an index or middle finger F, is shown in FIG. 1 where is has access to the first distal surface 26 of the first film layer 22 and further indicated by arrow R.

Figure 2:
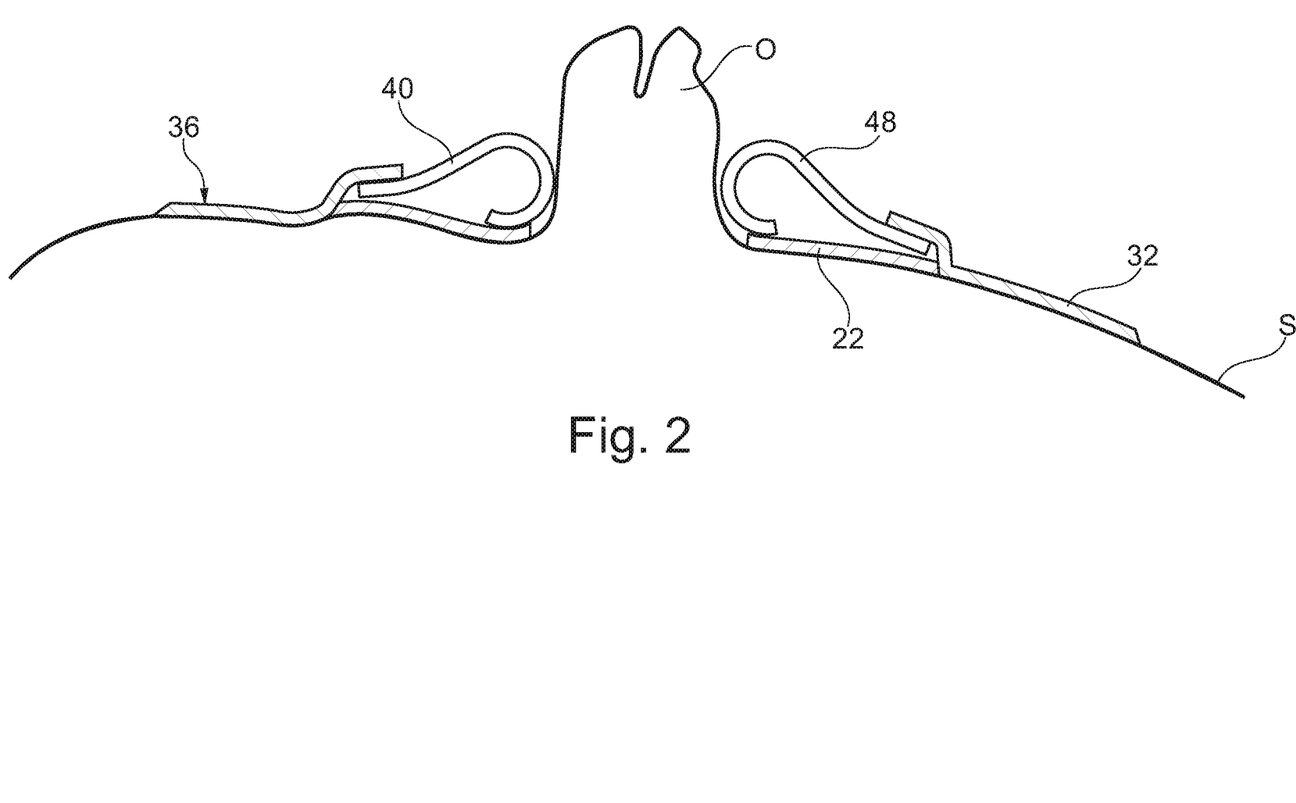
FIG. 2 is a cross-sectional view of one embodiment of a body side member in a second position, where it is applied to a user's skin around a stoma.

In the following, and with reference to FIGS. 1 and 2, one way of applying the body side member 20 to a user's skin surface S around a stoma O is described in more detail.

After preparation of the skin surface S surrounding the stoma O, the body side member 20 being in the first position is held with the fingers of one hand, such as by gripping at the second film layer with the thumb on the second proximal surface 34 and with the index finger on the second distal surface 36. In embodiments, each of the first proximal surface 24 and the second proximal surface 34 is provided with a film liner (not shown) protecting the adhesive on the respective surface 24, 34. The film liner on the first proximal surface 24 is removed with the fingers of the other hand. The first proximal surface 24 is brought into adhesive engagement with the peristomal area surrounding the stoma O by moving the body side member 20 in the direction of arrow Y such that the stoma O, or at least the stomal meatus M, is received in the through-going stoma opening 30 defined by the trumpet-shaped member 40.

The user applies finger pressure to the first distal surface 26 such that the adhesion of the first adhesive 28 provided on the first proximal surface 24 to the skin surface surrounding the stoma O is made as strong as possible. By providing finger pressure to the first distal surface 26 it is ensured that the first adhesive 28 flows well into the small pores and cracks of the peristomal skin surface, thereby improving the adhesive contact with the skin and in turn providing greater security against stomal output ending up on the proximal side of the first film layer 22. It follows, that a better and more evenly distributed application of finger pressure on the first distal surface 26 aids in providing the greater security. Embodiments of this disclosure provides a body side member 20 of an ostomy appliance wherein, in a first position of the body side member, the user has improved visibility and finger access to apply the first proximal surface 24 with the first adhesive 28 to the peristomal skin surface surrounding the stoma O. Thereby, the amount of time in which the finger pressure is applied can be prolonged without difficulty, in turn helping to improve the adhesive contact to the skin.

When the first adhesive 28 of the first proximal surface 24 has been brought into adhesive engagement with the peristomal skin surface, the user next removes a protective film liner (not shown) from the second proximal surface 34. In one embodiment, the film liner protecting the second adhesive 38 on the second proximal surface 34 is split into at least two portions. Thereby, each portion can cover less than an entirety of the second proximal surface 34 such that only a smaller section of the second adhesive 38 is exposed at a time. Finger pressure is then applied to the second distal surface 36 of the second film layer 32. The finger pressure provided on the second distal surface 36 causes the trumpet-shaped member 40 to convert into the second position of the body side member 20, whereby the second adhesive 38 on the second proximal surface 34 is brought into adhesive contact with the skin surface S of the user. One embodiment in which the body side member is in the second position is shown in FIG. 2. The trumpet-shaped member 40 is convertible between the first position and the second position in such a way that when the finger pressure applied to the second distal surface 36 exceeds a certain threshold, the trumpet-shaped member 40 "flips over" and assumes a shape having a bulge 48 surrounding the stoma O. The convertible nature of the trumpet-shaped member 40 allowing the "flipping over" and the shaping of the bulge 48 further imparts a tension in the second film layer 32 causing the second proximal surface 34 provided with the second adhesive 38 to be urged towards the skin surface. This urging of the second proximal surface 34 helps provide an improved adhesion of the second adhesive 38 to the skin surface. As described above with respect to the adhesion of the first adhesive 28 to the peristomal skin surface, the user similarly ensures improved adhesion of the second adhesive 38 by providing finger pressure to the second distal surface 36 to make the second adhesive 38 flow well into the small pores and cracks of the skin surface S.

In embodiments, the second adhesive 38 is provided on the second proximal surface 34 such that it surrounds (locates radially beyond an outer periphery of) the first film layer 22 when the body side member is in the second position. In embodiments, the second adhesive 38 is provided on the second proximal surface 34 such that it overlaps a portion of the first distal surface 26 of the first film layer 22 when the body side member is in the second position (FIG. 2).

In one embodiment, the trumpet-shaped member 40 is made from a resilient material. This is advantageous in providing the convertible nature of the trumpet-shaped member 40, and also in creating the tension effect in the second film layer 32. In one embodiment, the resilient material of the trumpet-shaped member 40 is a silicone material. In one embodiment, the resilient material of the trumpet-shaped member 40 is a polyurethane material. In one embodiment, the trumpet-shaped member 40 includes a reinforcement component. In one embodiment, the reinforcement component is embedded in the material of the trumpet-shaped member 40. In one embodiment, the reinforcement component is attached to an exposed surface of the trumpet-shaped member 40. In embodiments, the trumpet-shaped member 40 comprises one or more materials selected from the group of polyurethane elastomers.

In one embodiment, a first plane P1 of the first film layer 22 is parallel to a second plane P2 of the second film layer 32, the first and second planes P1, P2 being axially offset from each other seen along a central longitudinal axis A-A extending through the through-going stoma opening 30. Providing parallel planes P1, P2 is advantageous in ensuring equal access to distribution of finger pressure to the first distal surface 26 of the first film layer 22 all around the trumpet-shaped member 40 in the first position of the body side member 40. In one embodiment, a distance L1 between the first distal surface 26 of the first film layer 22 and the second proximal surface 34 of the second film layer 32 in the first position of the body side member 40 is from 10-40 mm. In one embodiment, the distance L1 is 12-30 mm, such as 20 mm.

In one embodiment, the first end portion 42 of the trumpet-shaped member 40 comprises a first flange extending radially away from a central longitudinal axis A-A extending through the through-going stoma opening 30. In one embodiment, the second end portion 44 of the trumpet-shaped member 40 comprises a second flange extending radially away from a central longitudinal axis A-A extending through the through-going stoma opening 30. The first and second flanges provides surfaces of the trumpet-shaped member 40 for attachment to the first and second film layers 22, 32 as described above. In addition, the first and second flanges provide backstops of the trumpet-shaped member 40, which help achieve the "flipping over" of the trumpet-shaped member 40 when finger pressure is applied to the second distal surface 36 and the body side member is shifted into the second position. In embodiments, the first and second flanges has an extent such as to cover 5-50% of a radial extent of the first distal surface 26 and/or the second proximal surface 34.

In one embodiment, the first adhesive 28 is in the form of a moldable ring. The adhesive material of the moldable ring can include a paste-type adhesive that is shapeable to be molded into a close fit with the stoma, and which subsequently keeps the molded shape. Suitable materials for the paste-type adhesive comprises adhesives of the types disclosed in WO 2010/069334. Providing the first adhesive 28 in the form of a moldable ring further improves the versatility of the body side member 20 and improves sealing characteristics and the security against leakage caused by stomal output.

Figure 3A:
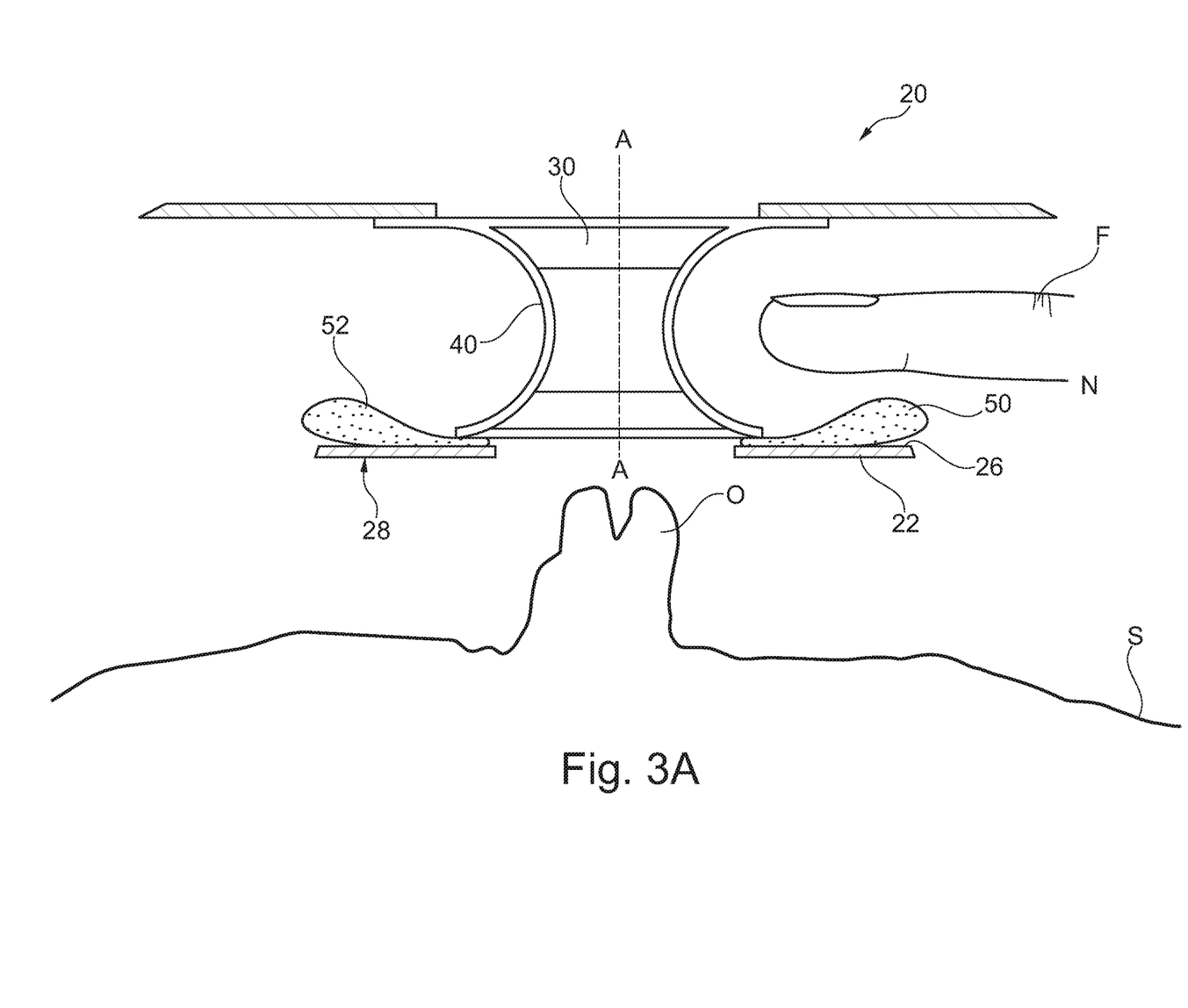
FIG. 3A is a cross-sectional view of one embodiment of a body side member in a first position, ready to be applied to the skin surface of a user around a stoma, and including a moldable adhesive material.
Figure 3B:
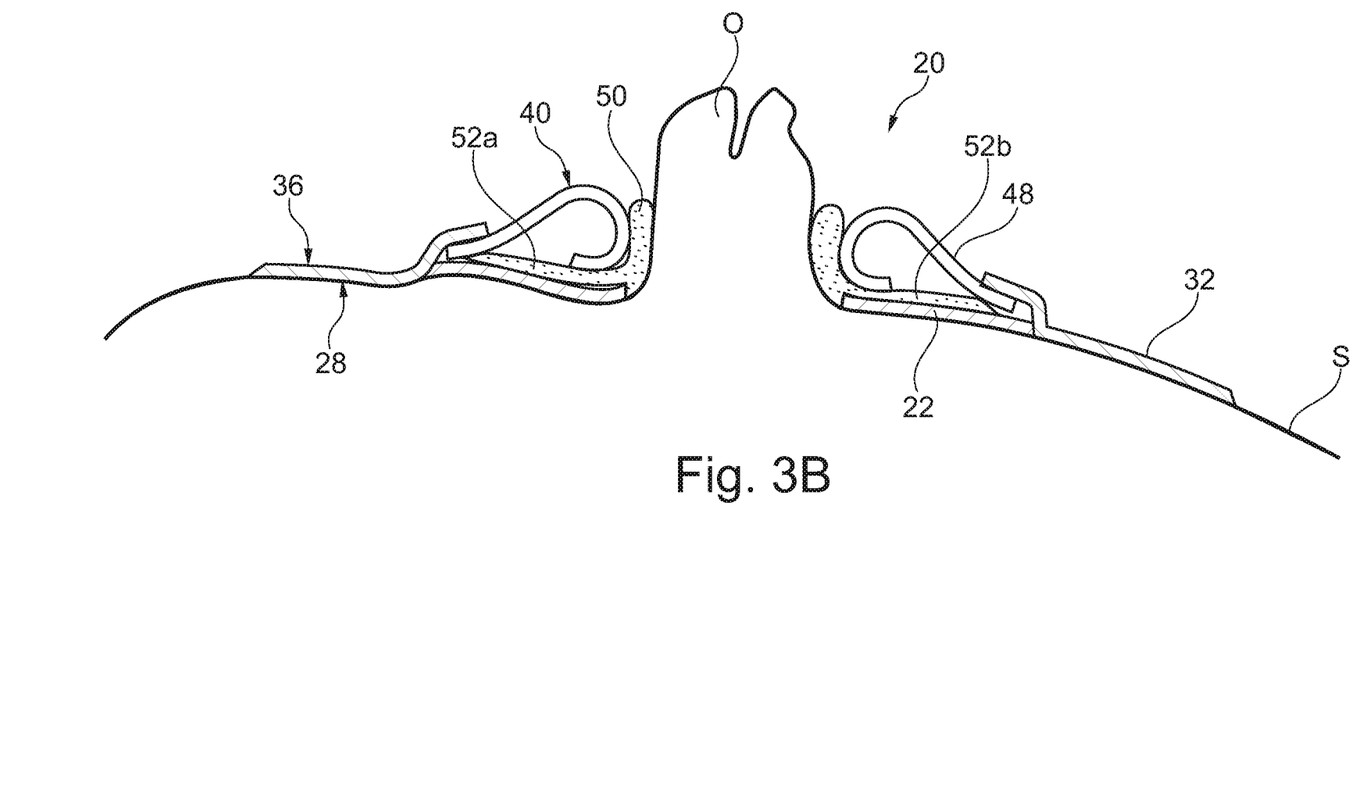
FIG. 3B is a cross-sectional view of one embodiment of a body side member in a second position, where it is applied to a user's skin around a stoma.

FIG. 3A illustrates one embodiment of a body side member 20 of an ostomy appliance including an amount of a moldable adhesive material 50 provided distal to the first distal surface 26 of the first film layer 22. The moldable adhesive material 50 is configured to be molded towards the central longitudinal axis A-A extending through the through-going stoma opening 30. In one embodiment, the moldable adhesive 50 is provided in a pocket 52 formed in the first film layer 22. In embodiments, an opening of the pocket 52 is at a portion of the pocket 52 radially closest to the central longitudinal axis A-A. In one embodiment, the adhesive 50 is provided in a pocket 52 formed by one or more film layers joined along an edge portion. In embodiments, the pocket 52 is located "on top of" the distal surface 26 of the first film layer 22. In embodiments, the pocket 52 is attached to the first film layer 22. In embodiments, the pocket 52 is attached to a radially innermost portion of the first film layer 22 (taken in relation to the central longitudinal axis A-A). In embodiments, the pocket 52 is attached to the trumpet-shaped member 40. In embodiments, the adhesive 50 is provided in two or more individual pockets 52a, 52b (FIG. 3B). In one embodiment, the pocket 52 is provided such that it covers part of, or all of, the first distal surface 26 of the first film layer 22. In embodiments, the pocket 52 is configured to allow for a finger of a user to enter between the first distal surface 26 of the first film layer 22 and a proximal surface of the pocket 52, such that the user can apply finger pressure to the first distal surface 26 for adhesive attachment to the skin surface. When the first adhesive is brought into adhesion with the skin surface, and with the body side member 40 still in the first position, the user can provide finger pressure to the pocket 52 containing the moldable adhesive material 50 and thereby squeeze out the moldable adhesive material 50 to create a seal against the stoma O.

FIG. 3B illustrates one embodiment of a body side member 20 in a view wherein the trumpet-shaped member 40 has been "flipped over" and wherein at least a portion of the adhesive material 50 has been squeezed out of the pocket 52 and against a surface of the stoma O. In this way, a sealing effect is achieved preventing stomal output from reaching and damaging the first adhesive layer 28.

Figure 4A:
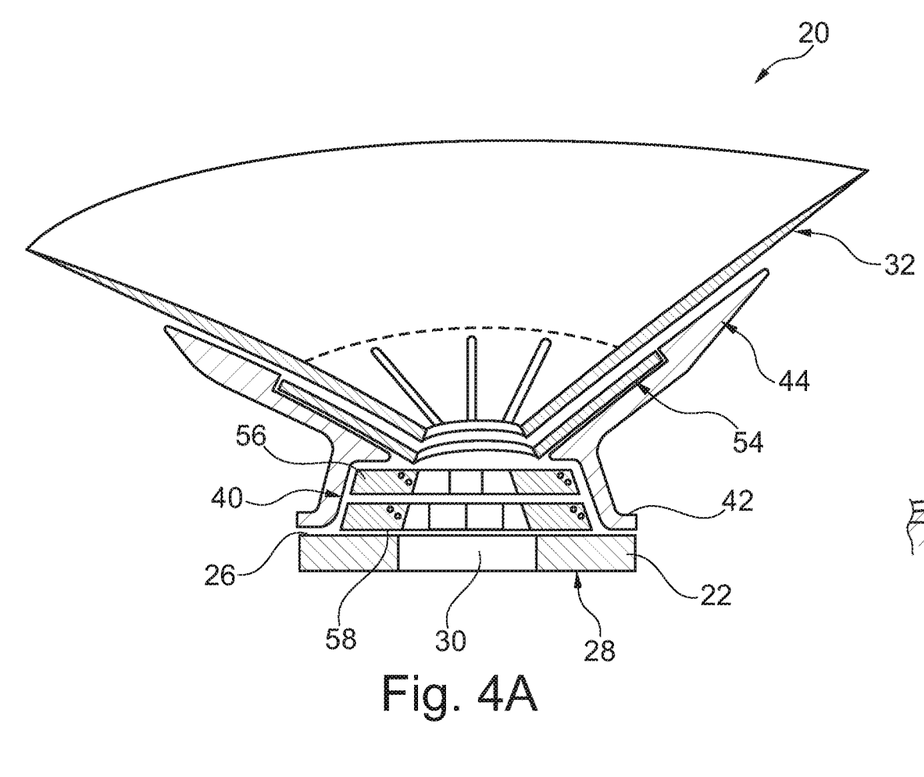
FIG. 4A is a schematic cross-sectional view of one embodiment of a body side member in a first position, including a reinforcement component and a fluid absorbing foam.

FIG. 4A illustrates one embodiment of a body side member 20 of an ostomy appliance. In the embodiment, illustrated in the first position of the body side member 40, a fluid absorbing foam 56 is provided within through-going stoma opening 30 and is attached at 58 to the first distal surface 26 of the first film layer 22. The foam can be attached by an adhesive or by a weld. The fluid absorbing foam 56 can be provided in a layered structure including two or more layers of foam, or it can alternatively be provided as a bulk portion of foam. The fluid absorbing foam 56 takes up moisture from the stoma, which causes the foam 56 to expand and adapt its shape to the stomal surface, thereby creating an improved sealing effect against stomal output. The fluid absorbing foam 56 can further be held in place around the stoma by an inner surface of the trumpet-shaped member 40. Suitable materials for the fluid absorbing foam 56 comprise hydrophilic polyurethane foams. FIG. 4A further shows an embodiment including a reinforcement component 54. The reinforcement component 54 can be provided to control the force of the urging of the second film layer 32 towards the skin surface of the user in the second position.

Figure 4B:
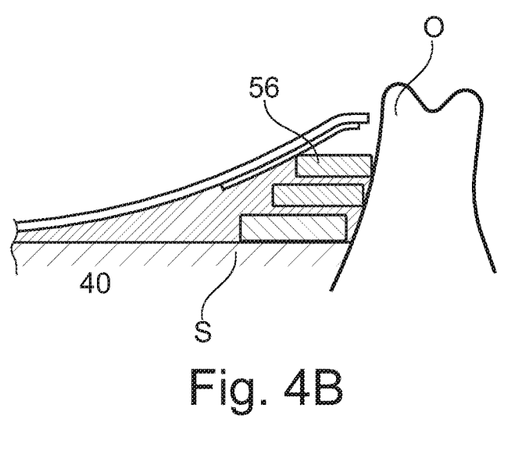
FIG. 4B is a schematic cross-sectional view of one embodiment of a body side member in a second position on a skin surface of a user.

FIG. 4B illustrates a section close to a stoma O of an embodiment of the body side member 40 in the second position on the skin surface S of a user, which embodiment includes a fluid absorbing foam 56. By moisture uptake, the foam 56 will adapt to the shape of the outer surface of the stoma O. A suitable material for the fluid absorbing foam 56 include open-celled urethane.

In embodiments, one half of a coupling for coupling the body side member 40 to a stomal output collecting bag (not shown) is attached to the second distal surface 36 of the second film layer 32 (FIG. 1). The other half of the coupling is attached to the stomal output collecting bag. This provides an ostomy appliance where a filled collection bag can readily be exchanged without having to exchange the body side member 40 each time the bag is filled. In one embodiment, the second distal surface 36 of the second film layer 32 is configured to form one half of an adhesive coupling interface. In other embodiments, a stomal output collecting bag is attached directly to second film layer 32 of the body side member 40 without first and second coupling halves or a coupling interface.

In another aspect, the present disclosure relates to a body side member of an ostomy appliance, comprising:

a first adhesive layer having a first proximal surface and a first distal surface provided around a through-going stoma opening of the body side member;

a film layer having a second proximal surface and a second distal surface, a second adhesive layer provided on the second proximal surface around the through-going stoma opening of the body side member; and a cone-shaped member having a first end portion attached to the first distal surface of the first adhesive layer and a second end portion attached to the second proximal surface of the film layer;

wherein a first plane of the first adhesive layer is parallel to a second plane of the film layer, the first and second planes being axially offset from each other seen along a longitudinal axis extending through the through-going stoma opening.

Embodiments of the present disclosure provides an advantageous body side member of an ostomy appliance in that it allows the user to apply a first portion of the adhesive interface (the first adhesive on the first film layer) in a first position of the member where full visibility and access to provide finger pressure is available. This is important in that improved adhesion of the first adhesive in the peristomal area is provides a greater security against the adhesive slipping the skin surface, potentially allowing stomal output to enter under the adhesive and create leakage. The body side member according to the disclosure intuitively guides the user to apply more pressure to the adhesive in the peristomal area. Moreover, the user's fingers do not come in contact with the stoma, which leads to improved hygiene. The "flipping over" function of the body side member informs the user when the product is applied and the created tension assists in providing better adhesion to the skin surface also of the second adhesive.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

The invention claimed is:

1. A body side member of an ostomy appliance, comprising:
   a first film layer having a first proximal surface, a first distal surface, a first stoma opening formed in the first film layer, and a first adhesive provided on the first proximal surface around a stoma opening and configured for attachment to skin around a stoma;
   a second film layer having a second proximal surface, a second distal surface, a second stoma opening formed in the second film layer, and a second adhesive provided on the second proximal surface around the second stoma opening; and
   a trumpet-shaped member having a proximal end portion attached to the first distal surface of the first film layer and a distal end portion attached to the second proximal surface of the second film layer, with a central portion of the trumpet-shaped member defining a stoma channel between the first film layer and the second film layer;
   wherein the proximal end portion and the distal end portion of the trumpet-shaped member are separated by a distance that is configured provide a user with finger access to the central portion of the trumpet-shaped member between the first distal surface of the first film layer and the second proximal surface of the second film layer, and wherein the second adhesive on the second proximal surface of the second film layer is attachable to the skin surrounding the first film layer to form a liquid seal around the first film layer and to prevent finger access between the first distal surface of the first film layer and the second proximal surface of the second film layer.

2. The body side member of claim 1, wherein the trumpet-shaped member is made from a resilient material.

3. The body side member of claim 1, wherein the distance between the proximal end portion and the distal end portion of the trumpet-shaped member is from 10-40 mm.

4. The body side member of claim 1, wherein the proximal end portion of the trumpet-shaped member comprises a first flange extending radially away from a central longitudinal axis extending through the stoma channel.

5. The body side member of claim 1, wherein the distal end portion of the trumpet-shaped member comprises a second flange extending radially away from a central longitudinal axis extending through the stoma channel.

6. The body side member of claim 1, wherein the first adhesive is a moldable ring of adhesive.

7. The body side member of claim 1, further comprising a fluid absorbing foam provided within the stoma channel and attached to the first distal surface of the first film layer.

8. The body side member of claim 1, wherein an amount of moldable adhesive material is provided distal to the first distal surface of the first film layer and is configured to be molded towards a central longitudinal axis extending through the stoma channel.

9. The body side member of claim 1, further comprising a moldable adhesive provided in a pocket in the first film layer.

10. The body side member of claim 1, wherein the trumpet-shaped member comprises a reinforcement component.

11. The body side member of claim 1, wherein each of the first proximal surface and the second proximal surface is provided with a film liner.

12. The body side member of claim 1, wherein a film liner on the protecting the second proximal surface of the second film layer is split into at least two individual portions.

13. The body side member of claim 1, wherein one half of a coupling for coupling the body side member to a stomal output collecting bag is attached to the second distal surface of the second film layer.

14. The body side member of claim 2, wherein the resilient material is a silicone material.

15. The body side member of claim 2, wherein the resilient material is a polyurethane material.

16. The body side member of claim 1, wherein a first plane of the first film layer is parallel to a second plane of the second film layer, the first and second planes being axially offset from each other seen along a longitudinal axis extending through the stoma channel.

17. A body side member of an ostomy appliance, comprising:
   a first adhesive layer having a first proximal surface and a first distal surface provided around a through-going stoma opening of the body side member and configured for attachment to skin around a stoma;
   a film layer having a second proximal surface and a second distal surface, a second adhesive layer provided on the second proximal surface around the through-going stoma opening of the body side member; and
   a cone-shaped member having: a proximal end portion attached to the first distal surface of the first adhesive layer; a distal end portion attached to the second proximal surface of the film layer; and a central portion defining a stoma channel between the first adhesive layer and the film layer
   wherein the film layer is a planar film layer and the first adhesive layer is planar and parallel to the planar film layer, with the first adhesive layer axially offset from the planar film layer along a longitudinal axis extending through the through-going stoma opening; and
   wherein, when the body side member is attached to the skin around the stoma, the second adhesive layer provided on the second proximal surface of the film layer engages and seals with the skin and a portion of the first distal surface of the first adhesive layer.

18. The body side member of claim 1, further comprising a moldable adhesive provided in two or more pockets in the first film layer.

19. The body side member of claim 1, wherein an opening of a pocket is located at a portion of the pocket radially closest to a central longitudinal axis A-A extending through the stoma channel.

20. The body side member of claim 19, wherein the pocket is attached to a radially innermost portion of the first film layer with respect to the central longitudinal axis A-A.

21. The body side member of any one of claim 1, further comprising a pocket attached to the trumpet-shaped member.

22. The body side member of claim 1, wherein the trumpet-shaped member is an annular tube having a sidewall that extends from the first film layer to the second film layer.

* * * * *

UNITED STATES PATENT AND TRADEMARK OFFICE
CERTIFICATE OF CORRECTION

PATENT NO. : 11,020,265 B2
APPLICATION NO. : 15/766366
DATED : June 1, 2021
INVENTOR(S) : Mireia Gordi Vila It is certified that error appears in the above-identified patent and that said Letters Patent is hereby corrected as shown below:

In the Specification

In Column 3, Line 1, delete "is" and insert -- it --, therefor.

In Column 4, Line 45-46, delete "body side member 40." and insert -- body side member 20. --, therefor.

In Column 4, Line 49, delete "body side member 40" and insert -- body side member 20 --, therefor.

In Column 5, Lines 44-45, delete "body side member 40" and insert -- body side member 20 --, therefor.

In Column 5, Line 58, delete "body side member 40," and insert -- body side member 20, --, therefor.

In Column 6, Line 12, delete "body side member 40" and insert -- body side member 20 --, therefor.

In Column 6, Line 19, delete "body side member 40" and insert -- body side member 20 --, therefor.

In Column 6, Lines 24-25, delete "body side member 40" and insert -- body side member 20 --, therefor.

In Column 6, Lines 29-30, delete "body side member 40" and insert -- body side member 20 --, therefor.

In the Claims

In Column 8, Line 11, in Claim 12, delete "protecting the", therefor.

In Column 8, Line 43, in Claim 17, delete "layer" and insert -- layer; --, therefor.

Signed and Sealed this
Twenty-first Day of February, 2023

Katherine Kelly Vidal
*Director of the United States Patent and Trademark Office*